(12) United States Patent
Briglin et al.

(10) Patent No.: US 10,175,198 B2
(45) Date of Patent: Jan. 8, 2019

(54) SYSTEM AND METHOD FOR OPTIMAL CHEMICAL ANALYSIS

(71) Applicant: INFICON, Inc., East Syracuse, NY (US)

(72) Inventors: Shawn Michael Briglin, Cazenovia, NY (US); Katherine Abigail Bartholomew, Syracuse, NY (US)

(73) Assignee: Inficon, Inc., East Syracuse, NY (US)

( * ) Notice: Subject to any disclaimer, the term of this patent is extended or adjusted under 35 U.S.C. 154(b) by 122 days.

(21) Appl. No.: 15/434,841

(22) Filed: Feb. 16, 2017

(65) Prior Publication Data

US 2017/0234834 A1    Aug. 17, 2017

Related U.S. Application Data

(60) Provisional application No. 62/295,818, filed on Feb. 16, 2016.

(51) Int. Cl.
| | | |
|---|---|---|
| *G01N 1/22* | (2006.01) | |
| *G01N 27/64* | (2006.01) | |
| *G01N 30/72* | (2006.01) | |
| *G01N 30/06* | (2006.01) | |
| *G01N 30/86* | (2006.01) | |
| *G01N 30/64* | (2006.01) | |

(52) U.S. Cl.
CPC ............. *G01N 27/64* (2013.01); *G01N 30/06* (2013.01); *G01N 30/7206* (2013.01); *G01N 30/8658* (2013.01); *G01N 1/2247* (2013.01); *G01N 1/2273* (2013.01); *G01N 2001/2285* (2013.01); *G01N 2030/067* (2013.01); *G01N 2030/642* (2013.01)

(58) Field of Classification Search
CPC .............. G01N 1/24; G01N 2001/028; G01N 2001/2223; G01N 2001/022; G01N 1/22; G01N 1/14; G01N 1/2226; G01N 15/06; G01N 1/2247; G01N 1/2273; G01N 2001/2285; G01N 33/0057
See application file for complete search history.

(56) References Cited

U.S. PATENT DOCUMENTS

| | | | | |
|---|---|---|---|---|
| 2,947,166 A | * | 8/1960 | Palmer ................. | G01M 3/002 73/335.02 |
| 3,786,675 A | * | 1/1974 | Delatorre ............. | G01M 3/002 340/605 |

(Continued)

OTHER PUBLICATIONS

HPMS & Separations Technology; © 2017 908 Devices; retrieved from the Internet: http://908devices.com/technology/.

(Continued)

*Primary Examiner* — David A Rogers
(74) *Attorney, Agent, or Firm* — Barclay Damon LLP

(57) ABSTRACT

A system and method for chemical analysis are described herein. The system includes a probe, a sample collection cartridge, and a chemical analyzer. The probe is configured to collect the optimal amount of sample for a future analysis and to store this chemical sample in the sample collection cartridge. The probe also collects sample data. The chemical analyzer is configured to determine the optimal analysis settings based on the sample data and analyze the chemical sample stored in the sample collection cartridge based on the optimal analysis settings.

20 Claims, 15 Drawing Sheets

(56) References Cited

U.S. PATENT DOCUMENTS

| | | | | |
|---|---|---|---|---|
| 4,580,440 | A * | 4/1986 | Reid | G01V 9/007 73/31.07 |
| 4,819,477 | A * | 4/1989 | Fisher | G01N 1/2258 73/28.01 |
| 4,909,090 | A * | 3/1990 | McGown | G01N 1/2214 73/863.12 |
| 5,092,218 | A * | 3/1992 | Fine | G01N 1/02 436/156 |
| 5,336,467 | A | 8/1994 | Heidt et al. | |
| 5,526,280 | A * | 6/1996 | Consadori | G01N 27/16 340/632 |
| 5,859,375 | A | 1/1999 | Danylewych-May et al. | |
| 5,895,375 | A | 4/1999 | Wilcox et al. | |
| 5,988,002 | A | 11/1999 | Danylewych-May et al. | |
| 6,167,767 | B1 | 1/2001 | Mengel et al. | |
| 6,269,703 | B1 * | 8/2001 | Bowers | G01N 1/22 73/863.12 |
| 6,321,609 | B1 | 11/2001 | Mengel et al. | |
| 6,446,514 | B1 | 9/2002 | Danylewych-May et al. | |
| 6,651,520 | B1 * | 11/2003 | Allen | G01N 1/2214 137/512.15 |
| 6,672,129 | B1 * | 1/2004 | Frederickson | A61M 15/02 347/20 |
| 6,828,795 | B2 * | 12/2004 | Krasnobaev | G01N 27/622 324/464 |
| 6,861,646 | B2 * | 3/2005 | Motchkine | G01N 1/02 250/281 |
| 6,895,804 | B2 * | 5/2005 | Lovell | G01N 1/2202 73/31.05 |
| 7,100,461 | B2 * | 9/2006 | Bradley | G01N 1/02 73/864.33 |
| 7,115,859 | B2 | 10/2006 | Cornish | |
| 7,168,298 | B1 | 1/2007 | Manginell et al. | |
| 7,357,044 | B2 | 4/2008 | Sleeman et al. | |
| 7,600,439 | B1 | 10/2009 | Patterson et al. | |
| 7,726,211 | B2 * | 6/2010 | Montefusco | G01N 1/2205 73/863.41 |
| 7,836,751 | B2 * | 11/2010 | Marra | B60H 1/008 73/28.02 |
| 7,841,244 | B2 | 11/2010 | Barket, Jr. et al. | |
| 7,905,154 | B2 * | 3/2011 | Jones, Jr. | A22B 5/007 73/23.34 |
| 7,992,424 | B1 | 8/2011 | Grossenbacher | |
| 7,997,119 | B2 * | 8/2011 | Wu | G01N 1/14 324/239 |
| 8,113,069 | B2 * | 2/2012 | Settles | G01N 1/2226 73/863 |
| 8,146,448 | B2 | 4/2012 | Briscoe et al. | |
| 8,161,797 | B1 * | 4/2012 | Genovese | G01N 1/22 73/31.01 |
| 8,193,487 | B2 | 6/2012 | Briglin et al. | |
| 8,272,280 | B2 * | 9/2012 | Jones, Jr. | A22B 5/007 73/23.34 |
| 8,307,723 | B2 * | 11/2012 | Novosselov | G01N 1/2202 73/864 |
| 8,377,711 | B2 * | 2/2013 | Henry | G01N 21/658 356/36 |
| 8,525,111 | B1 | 9/2013 | Brown et al. | |
| 8,555,701 | B1 * | 10/2013 | Sacerio | G01N 27/14 73/31.05 |
| 8,578,796 | B2 | 11/2013 | Cho | |
| 8,607,616 | B2 * | 12/2013 | Marra | G01N 1/2202 73/28.02 |
| 8,646,340 | B2 * | 2/2014 | Zhang | G01N 1/24 73/863.11 |
| 8,756,975 | B2 * | 6/2014 | Wu | G01N 1/14 73/31.05 |
| 9,080,930 | B2 * | 7/2015 | Bakker | F23G 5/50 |
| 9,086,341 | B2 * | 7/2015 | Tsai | G01N 1/2208 |
| 9,335,236 | B2 * | 5/2016 | Bry | G01N 1/2211 |
| 9,360,491 | B2 * | 6/2016 | Sever | G01N 33/54366 |
| 9,410,871 | B1 * | 8/2016 | St Amant, III | G01N 1/2247 |
| 9,423,388 | B2 * | 8/2016 | Terada | G01N 1/2202 |
| 9,772,271 | B2 * | 9/2017 | Peacock | G01N 15/06 |
| 2006/0150707 | A1 * | 7/2006 | Rolff | G01M 3/207 73/1.05 |
| 2007/0039377 | A1 * | 2/2007 | Bohm | G01M 3/207 73/40.7 |
| 2007/0114389 | A1 * | 5/2007 | Karpetsky | H01J 49/142 250/288 |
| 2007/0158447 | A1 * | 7/2007 | Bunker | G01N 1/02 239/1 |
| 2009/0188302 | A1 * | 7/2009 | Rolff | G01M 3/207 73/40.7 |
| 2015/0143929 | A1 * | 5/2015 | Volckens | G01N 1/2202 73/863.11 |

OTHER PUBLICATIONS

Inficon HAPSITE ER Chemical Identification System; © 2009 INFICON; retrieved from the Internet: (http://products.inficon.com/GetAttachment.axd?attaName=b0ddf534-db3e-4920-b9c1-ec872bc28a4d).

* cited by examiner

SYSTEM AND METHOD FOR OPTIMAL CHEMICAL ANALYSIS

CROSS-REFERENCE TO RELATED APPLICATIONS

This application claims the benefit of and priority to U.S. Provisional Patent Application Ser. No. 62/295,818, filed Feb. 16, 2016 and entitled "SAMPLE COLLECTOR AND METHOD FOR OPTIMAL CHEMICAL COLLECTION AND ANALYSIS," the entirety of which is incorporated herein by reference.

BACKGROUND OF THE INVENTION

The subject matter disclosed herein related to the field of chemical detection and more particularly to a chemical analysis system comprising a chemical sample collector that is operated remotely from a chemical analyzer.

In some situations, emergency response personnel need to quickly and accurately identify and quantify chemical hazards. These circumstances include both accidental discharges of toxic or industrial chemicals and deliberate releases, such as in terrorist attacks or chemical warfare. The need for rapid assessment of chemical health risks, combined with the unstable nature of many chemicals of concern, often mandate that the analysis occur at, or as near as possible to, the site of a chemical release. A number of chemical detector technologies have been developed to address potential chemical hazards that may exist in air, on surfaces, or in water. These technologies include Mass Spectrometers (MS), Gas Chromatograph/Mass Spectrometers (GC/MS), Ion Mobility Spectrometers (IMS), along with optical technologies such as Fourier Transform Infrared Spectroscopy (FTIR) and Raman, among others. Some of these technologies have been miniaturized and ruggedized to the extent that handheld analyzers can be carried directly into environments of chemical contamination. Some of these approaches are also based on small mass spectrometers (MS), as described in U.S. Pat. No. 8,525,111; U.S. Pat. No. 7,115,859; and 908devices.comitechnology/, the entirety of which are incorporated herein by reference. However, the designers of these and other miniaturized systems have often been forced to make sacrifices in analytical performance in order to minimize system size and weight. These sacrifices can negatively impact system performance, particularly in situations requiring highly definitive chemical analyses, such as forensics and attribution. Typically, miniature analyzers are too expensive for the resulting measure of analytical performance provided, and this compromise in performance is not acceptable in many emergency response scenarios. Slightly larger and higher fidelity chemical analyzers have been developed for field applications. Although these field analyzers can be moved into a contaminated hazmat area, the size, weight, and limited battery life or power requirements of these field analyzers typically leave these instruments to be stationed in safe areas just outside the contaminated zone. These include for example GC/MS analyzers such as the Bruker E2M and the INFICON HAPSITE.

In emergency response scenarios requiring a high fidelity analysis, a remote sample collector is typically transported into the contaminated hot zone to obtain a sample to be analyzed by a high performance chemical analyzer stationed in a nearby field lab. Although the analysis is delayed while the exterior of the sample collector is decontaminated, if necessary, and transported out of the hot zone, this process permits a high performance analysis under more controlled conditions than are typically possible directly at the chemical source. Systems and devices that make use of this remote sampling paradigm are taught in U.S. Pat. No. 6,167,767; U.S. Pat. No. 6,321,609 B1; U.S. Pat. No. 6,446,514; U.S. Pat. No. 5,988,002; U.S. Pat. No. 5,895,375; U.S. Pat. No. 8,146,448; U.S. Pat. No. 8,578,796; U.S. Pat. No. 7,600,439; U.S. Pat. No. 7,841,244; U.S. Pat. No. 5,859,375; U.S. Pat. No. 7,357,044; and U.S. Pat. No. 5,336,467, the entirety of which are incorporated herein by reference.

Along with the performance improvements garnered by bringing the sample to a higher performance analyzer, there are also benefits in carrying a small, lightweight, low power, and low cost sample collector. Remote sample collection affords logistical savings by allowing sample collection in multiple locations simultaneously and analyzing these samples at one nearby chemical analyzer. Despite the aforementioned advantages, chemical analysis systems employing remote sample collection suffer from performance issues related to the decoupling of collection from analysis. For example, the sample can be collected in a non-optimal time and place. Many sources, such as gas and vapor leaks, produce turbulent plumes with a high degree of spatiotemporal variability in vapor phase concentration. Because of this variation, it is possible to collect sample air near a vapor point source and still miss virtually the entire chemical sample. Even non-stochastic sources of concentration variation, such as advection, can cause a sample collector to entirely miss collection from a point source. Collecting samples in the wrong location can thus lead to incorrect determinations on site safety with respect to toxic chemicals.

In another example of a disadvantage of the decoupling between collection and analysis, an insufficient quantity of a sample can be collected even when collecting in an optimal location, if for example the collection time was too short. Collecting an insufficient quantity of a sample will often result in a low signal-to-noise ratio (SNR) in the chemical analysis and thus missed detections or incorrect identifications leading to false alarms.

In yet another disadvantage, an excess amount of a sample can be collected. Collecting excess sample can generate outcomes that are as detrimental to the quality of the chemical analysis as those that occur when collecting too little sample. GC columns, and particularly the narrow bore thin phase columns used for very high speed chromatography, have very limited capacity. Overloading the columns with excess sample causes peak broadening and decreased GC separation performance. Decreased separation performance may defeat a primary purpose of the GC column, which is to separate chemicals of interest from interfering chemicals in a background matrix. This reduces the quality of analysis, and may lead to missed detections or false alarms. Other components in the analyzer, such as the MS electron multiplier and electrometer, may also have limited dynamic range. In applications with very high speed GC separations and sharp GC peaks, fast scanning of the mass spectrometer is required to generate enough data points for accurate integrations of the MS data points collected across a GC peak. In practice, this fast scanning can result in an effective dynamic range of as little as 2 or 3 decades in a field analyzer. Thus, it is important to collect the optimal mass of sample when the sample is to be subjected to the high speed analysis desired in typical hazardous chemical scenarios.

In yet another disadvantage of existing systems, with only one opportunity to analyze a collected sample, suboptimal instrumental settings may be used to analyze a sample having a mass outside of the optimal range. These suboptimal settings can lead to a poor quality analysis with lower signal to noise ratios and reduced GC peak integration precision than which would be achieved if the components were adjusted to more optimally match the quantity of collected sample.

A further disadvantage of the decoupling of collection from analysis is that collected samples may need to be decontaminated before being removed from the hazmat hot zone and transported to the analyzer. This requires decontamination of the exterior of a sample cartridge prior to analysis. Inadequate knowledge with respect to the levels of VOCs in the hazardous sample collection environment may lead to unnecessary or inadequate decontamination procedures. Excessive decontamination procedures may even degrade some low stability chemical samples.

The HAPSITE ER (products.inficon.com/GetAttachmentaxd?attaName=b0ddf534-db3e-4920-b9c1-ec872bc28a4d) discloses a basic form of reactive sample collection. In this embodiment, the instrument makes use of the same MS that the system uses for GC/MS analysis. In a particular configuration of inlet valves, sample air from an attached sample line is pulled directly to the MS for analysis. The system informs the operator when the sample line is in an acceptable position for good sample collection, meaning that the sum of all MS ions detected for all of the volatile organic compounds (VOCs) measured by the MS are within an acceptable range. The user then switches the instrument into a sampling mode, which has a different configuration of inlet valves, and a predefined volume of sample air is collected on an internal sample collector. The system collects a volume of air rather than a predefined mass of chemical sample. If the sample vapor concentration changes during the collection interval, such as due to wind, turbulence, or slight movement of the sample line with respect to a point source, a suboptimal quantity of sample, such as too much or too little, is collected despite collection of the intended volume of air. A further disadvantage of this approach is that the entire instrument must be carried into the hot zone since the same MS is used to provide the level indication that is used for the full chemical analysis.

Another form of reactive sampling using a surface condition indicator for feedback during a sample collection is taught by U.S. Pat. No. 8,193,487, the entirety of which is incorporated herein by reference. The surface condition indicators are chemicals monitored with the MS itself during the sample collection. This technique is indicative of a surface condition such as the temperature of a contaminated soil surface rather than more directly indicative of concentrations of the target chemicals in air. This technique also uses the same MS for feedback preventing it from being used in a lightweight, low cost, remote sample collector. U.S. Pat. No. 7,992,424, the entirety of which is incorporated herein by reference, teaches adjusting instrumental parameters for a GC/MS analysis based on an estimate of the amount of a collected sample by diverting sample to a membrane inlet to the MS prior to GC analysis. This technique helps optimize the GC analysis for variations in sample quantity. However, this technique cannot be made remote from the analyzer and provides no mechanism to obtain a sample in the best location or to collect an optimal sample quantity.

Another form of reactive sample collection is described by U.S. Pat. No. 7,168,298, the entirety of which is incorporated herein by reference. A mass sensitive sample collection device includes a pivot-plate resonator with a chemically sensitive coating. During sampling, the resonator changes frequency which corresponds to a change in the total collected mass of the sample. Using the sample collection device as the detector requires that any sample detected is also collected. This approach can be disadvantageous because the system cannot scan an area for a plume or point source of contamination prior to initiating collection, which can lead to collection of excess background chemicals. Additional disadvantages with this approach are that the micro resonators are expensive relative to glass or metal tubes used for most types of field sample collection, have poorly swept geometries, meaning that they are not easily coupled to a GC system which leads to poor chromatographic peak shapes, and, by nature of the microelectromechanical systems (MEMS) design, have very limited sample capacity. In some embodiments, limited sample capacity negates the benefits from collecting an optimal amount of sample. Additionally, commonly used adsorbents for the collection of toxic industrial chemicals (TICs) and Chemical Warfare Agents (CWAs), such as graphitized carbon, are granular and do not lend themselves to forming the tightly coupled thin films required for the acoustic coupling of the adsorbent/absorbent to the resonator. Thus, the device must collect samples using inferior collection materials.

BRIEF SUMMARY OF THE INVENTION

A system and method for chemical analysis are described herein. The system includes a probe, a sample collection cartridge, and a chemical analyzer. The probe is configured to collect the optimal amount of sample for a future analysis and to store this chemical sample in the sample collection cartridge. The probe also collects sample data. The chemical analyzer is configured to determine the optimal analysis settings based on the sample data and analyze the chemical sample stored in the sample collection cartridge based on the optimal analysis settings.

In one embodiment, a chemical analysis system is described. The chemical analysis system includes a probe including a photo ionization detector (PID) module configured to measure vapor concentration and a microcontroller. The chemical analysis system also includes a chemical analyzer and a sample collection cartridge configured to removable coupled to each of the probe and the chemical analyzer, respectively. The sample collection cartridge includes a sample retention device configured to store a chemical sample and a memory. The probe is configured to determine an optimal sample collection location. When the sample collection cartridge is coupled to the probe, the probe is configured to collect a chemical sample in the sample collection cartridge and the microcontroller is configured to collect sample data during sample collection and store the sample data in the memory. When the sample collection cartridge is coupled to the chemical analyzer, the chemical analyzer is configured to determine optimal analysis settings based on the stored sample data and analyze the chemical sample using the determined optimal analysis settings.

In another embodiment, a probe for a chemical analyzer is described. The probe includes a photo ionization detector (PID) module configured to measure vapor concentration of a chemical sample and a removable sample cartridge including an inlet port and a sample retention device. A sample pump is operatively coupled to the removable sample cartridge and configured to draw a chemical sensor through the inlet port and into the sample retention device. The probe additionally includes a microcontroller and a memory configured to store a reference table of target sample masses.

The microcontroller is configured to determine an optimal sample collection location, monitor sample collection, determine sample data, and discontinue sample collection based on the sample data and the reference table.

In yet another embodiment, a method of optimizing chemical sample analysis with a chemical analysis system is described. The chemical analysis system includes a probe, a sample collection cartridge, and a chemical analyzer. The probe includes a photo ionization detector (PID) module and a microcontroller and the sample collection cartridge includes a sample retention device and a memory. The method includes locating, via the PID module, an optimal sample collection location. The method further includes collecting and storing a chemical sample in the retention device when the sample collection cartridge is retained within the probe, collecting, via the microcontroller, sample data, and storing the sample data in the memory.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION OF THE INVENTION

Figure 1:
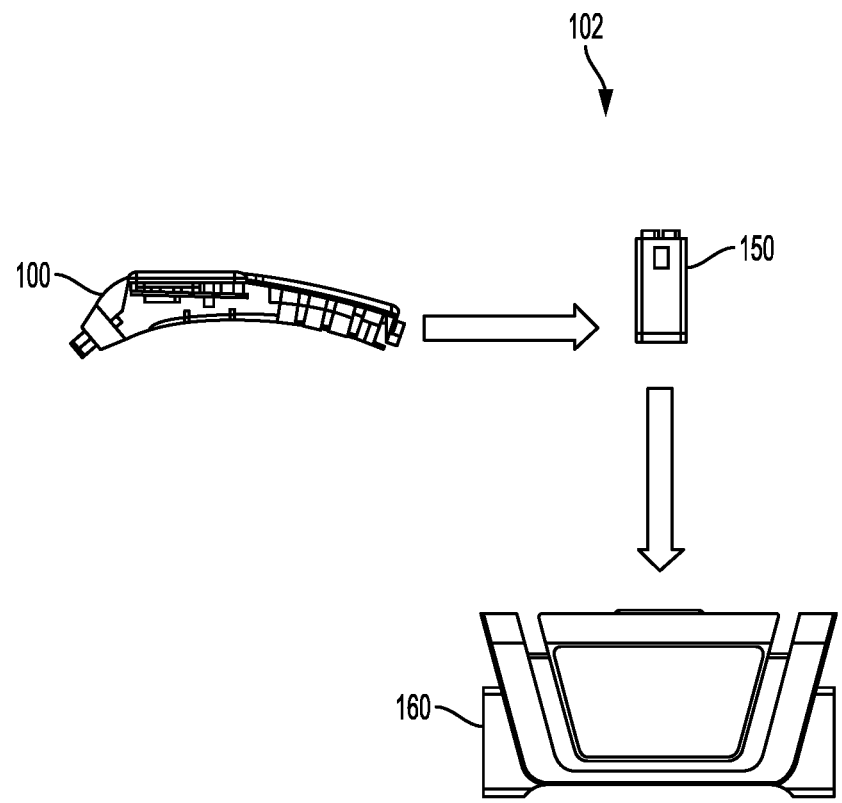
FIG. 1 is an illustration of an embodiment of a chemical analysis system including a sample collection probe, a sample collection cartridge, and an analyzer.

FIG. 1 illustrates a remote sampling system 102 including a sample collection probe 100, a sample collection cartridge 150, and a chemical analyzer 160. The sample collection cartridge 150 is configured to be removably coupled to either the sample collection probe 100 and to the chemical analyzer 160, respectively.

Figure 2:
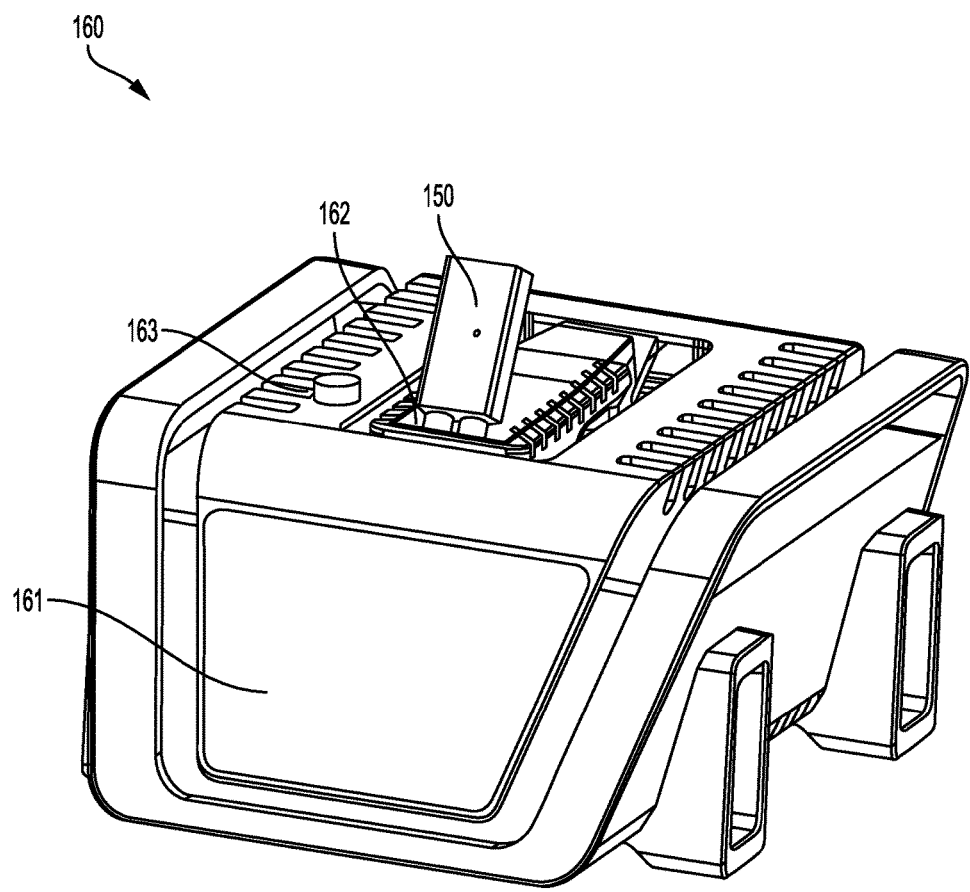
FIG. 2 is an illustration of an embodiment of a chemical analyzer.

FIG. 2 illustrates an embodiment of a chemical analyzer 160. In an embodiment, the chemical analyzer 160 is a gas chromatograph/mass spectrometer (GC/MS). The chemical analyzer 160 is typically a GC/MS, but can be a GC with any other detector type such as a flame ionization detector (FID) or a flame photometric detector (FPD). Alternatively, the chemical analyzer 160 can be any alternative high performance chemical measurement system, such as a chemical analyzer using Fourier transform infrared spectroscopy (FTIR) or Raman. Chemical analysis could include identification, quantitation, class identification, or any combination of these or any other analysis necessary to make decisions on health and safety of a chemical hazard or event. A controller (not shown) controls the operation of the chemical analyzer 160. The controller can include a microprocessor, microcontroller, programmable-logic device (PLD), programmable logic array (PLA), programmable array logic (PAL), field-programmable gate array (FPGA), application specific integrated circuit (ASIC), or other computing or logic device programmed, wired, or configured to perform functions described herein. Memory (not shown) can be coupled to the controller. Memory can be any suitable type of memory.

The chemical analyzer 160 includes a touchscreen user interface 161 and a sample interface 162 for coupling to the sample collection cartridge 150. The sample interface 162 has a pneumatic component (not shown), which facilitates transfer of a chemical sample from the sample collection cartridge 150 to the chemical analyzer 160. The chemical analyzer 160 additionally includes an auxiliary gas port 163 for use in calibrating the PID contained within the sample collection probe.

Figure 3:
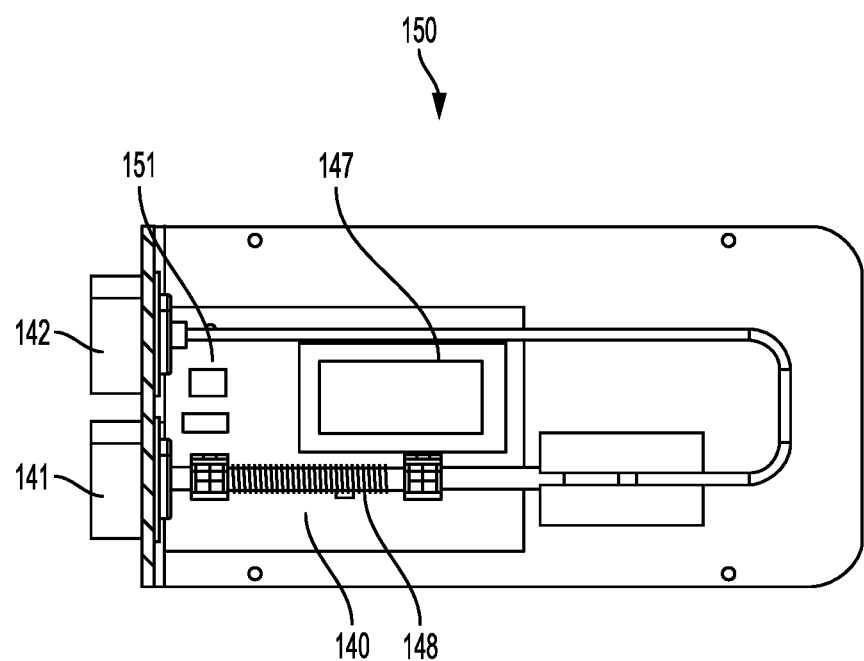
FIG. 3 is a section view of the sample collection cartridge of FIG. 4.
Figure 4:
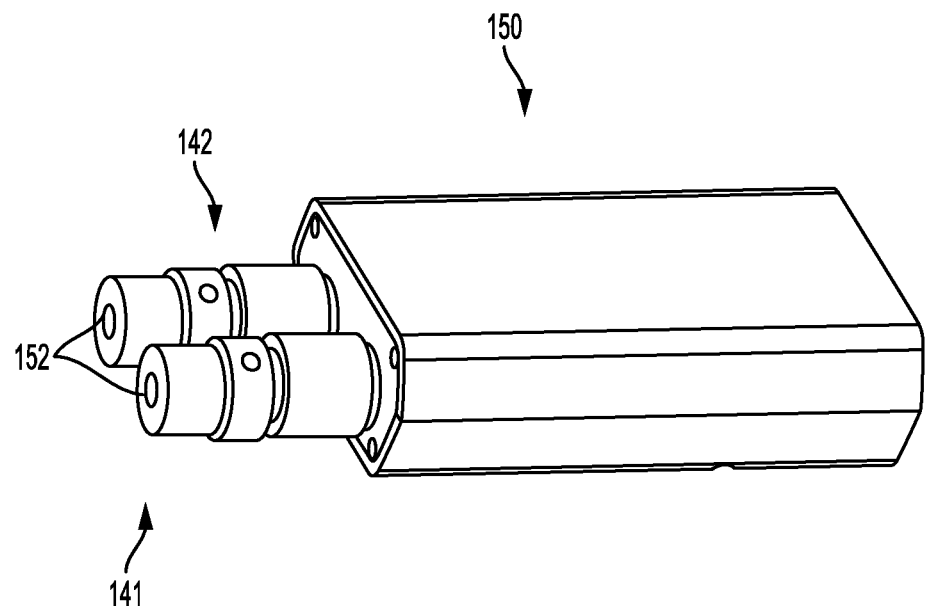
FIG. 4 is an illustration of an embodiment of a sample collection cartridge.

FIGS. 3 and 4 illustrate an embodiment of a sample collection cartridge 150. As illustrated in FIG. 3, the sample collection cartridge 150 can include a communication system, such as an antenna 147, and a memory device 151. Alternatively, the sample collection cartridge 150 can be coupled to a cloud storage system (not shown). The sample collection cartridge 150 includes at least one sample retention device 140, such as an adsorbent bed, using a sample loop or packed bed of sample collection media to capture chemical samples from air. In the illustrated embodiment, the sample collection cartridge 150 employs a bed of a chemical adsorbing or absorbing media, such as Tenax® TA or Carbopack™ B, or a plurality of such beds arranged in order of increasing adsorbent strength in the direction that air is drawn during the sampling event. As air is drawn through the sample collection cartridge 150 from the inlet port 141, chemicals are captured from the air in this adsorbent bed 140 before it exhausts though the exhaust port 142. In another embodiment, the sample collection cartridge 150 utilizes a sample loop (not shown) instead of an adsorbent/absorbent media. The sample loop variant of the sample collection cartridge 150 traps the chemical sample in a volume defined between two valves (not shown) positioned at the ends of the adsorbent bed 140 shown in FIG. 3. A heating coil 148 is positioned around the tube in the region of the adsorbent bed 140.

The sample collection cartridge 150 is configured to removably couple to the sample collection probe 100 and to the chemical analyzer 160. In an embodiment, the sample collection cartridge 150 can be removed or decoupled without tools. Following decoupling of the sample collection cartridge 150 from either the probe 100 or the chemical analyzer 160, the input 141 and output 142 ports of the sample collection cartridge 150 can be capped with caps 152, as illustrated in FIG. 4, to ensure sample integrity if the sample is to be stored for prolonged periods prior to analysis. In this embodiment, the caps 152 grab features at ports 141, 142 of the sample collection cartridge 150 via a ball spring (not shown) and seal the end of the sample retention device 140 to prevent undesired gases from reaching or leaving the adsorbent bed contained in the sample retention device 140. This sealing could also be accomplished via a self-sealing means such as the self-sealing means taught by U.S. Pat. No. 6,321,609, the entirety of which is incorporated herein by reference. However, such self-sealing means has the disadvantage of potentially leaving elastomer in the sample pathway. Leaving the elastomer in the sample pathway can be detrimental to collection and analysis because sample gases can partition into the elastomer during these processes causing loss of sample. Sealing the sample collection cartridge 150 ports 141, 142 also facilitates cleaning and decontamination of the sample collection cartridge 150 prior to its removal from a hot zone or sample collection area for analysis in the chemical analyzer 160.

Figure 5:
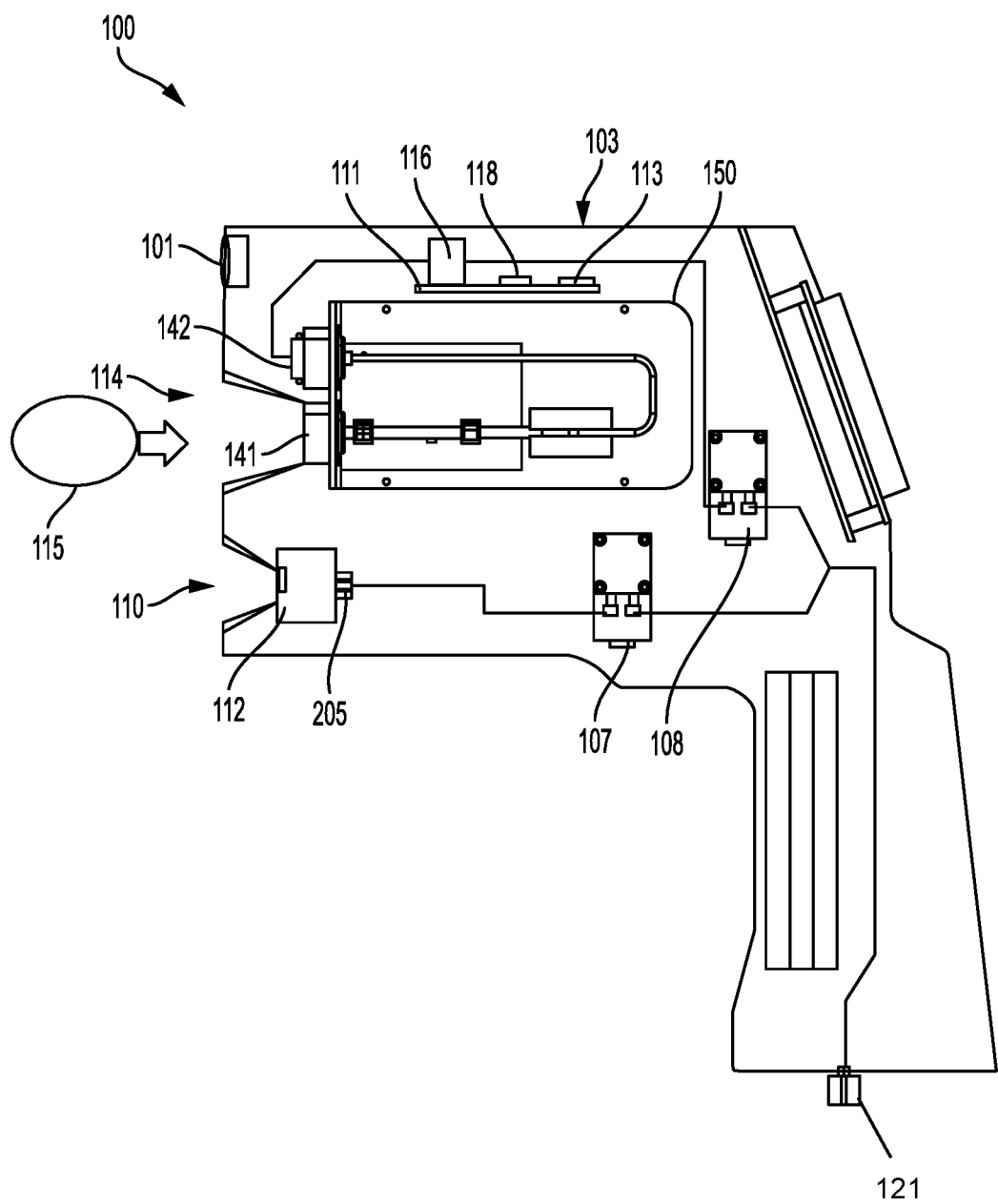
FIG. 5 is an illustration of the sample collection probe of FIG. 1.

An embodiment of a sample collection probe 100, with the sample collection cartridge 150 retained therein, is illustrated in FIG. 5. The sample collection probe housing 103 has a first recess or opening 114. When the sample collection cartridge 150 is retained in the sample collection probe 100, the input port 141 of the sample retention device 140 (e.g., adsorbent bed or sample loop) accesses the air environment 115 of an area of interest, either directly or via another functional attachment (not shown), such as a filter, a reactor, or a physical guard where the connection is made directly to the input port 141 of the sample collection cartridge 150. Filters (not shown) can be positioned in the first opening 114 and can be, for example, a particulate filter, a water separating membrane such as Gore-tex, or a reactive material such as a silanizing agent or silver fluoride. Silver fluoride filters are used to chemically convert a class of highly toxic yet low volatility compounds into higher volatility analogues for improved detection. Another port 142 of the sample cartridge 150 is in fluidic connection with a first sample pump 108. When powered, the first pump 108 draws environmental air 115 into the sample retention device 140 (e.g., adsorbent bed), where it is stored for later analysis. An advantage of this approach is that cold spots and points of carryover are not in line with the input side of the sample pathway.

In an embodiment, a Photo Ionization Detector (PID) module 112 is positioned within the housing 103 at a second opening 110 in the housing 103 adjacent to the first opening 114, where a sample is collected in the sample retention device 140. In an embodiment, the centers of the openings 110, 114 are as close as possible but do not share the same opening so as to reduce sample condensation and carryover on the surfaces of the first opening 114 when very high concentrations of the sample are encountered during PID screening of an area but prior to initiating a sample collection onto the sample retention device by activating the sample pump 108. In an embodiment, the centers of these openings 114 and 110 are within 1 inch to reduce the effects of local fluctuations in sample concentration, such as near a pinhole leak in a chemical storage vessel. Positioning the second opening 110 to the PID module 112 and the first opening 114 to the sample collection cartridge 150 in tight proximity ensures that these subassemblies experience the same concentration, even in a highly spatially structured vapor or gas plume. Air is exhausted through the exhaust 121.

While the chemical sensor on the sample collection probe 100 has been described above as a photo ionization detector (PID), it is to be understood that any other suitable type of compact, broadly responsive chemical sensor could be used. Examples of other broadly responsive chemical sensors include coated surface acoustic wave (SAW) gas sensors and tin oxide (SnOx) sensors, among others.

The sample collection probe 100 also includes a small second sample pump 107, a microcontroller 113, and an air flow sensor 116. In an alternative embodiment, one or both of the pump 108 and the second sample pump 107 can be a fan. In yet another embodiment, not shown, a fan can be positioned between the inlet port 110 and the PID module 112 to improve airflow to the PID module 112. In addition, an exhaust pump or fan (not shown) can be coupled to the exhaust port 121 to assist in expelling air. Further, the probe 100 can include a communication system, such as a near field antenna 111. The probe 100 can also include memory 118.

Figure 6:
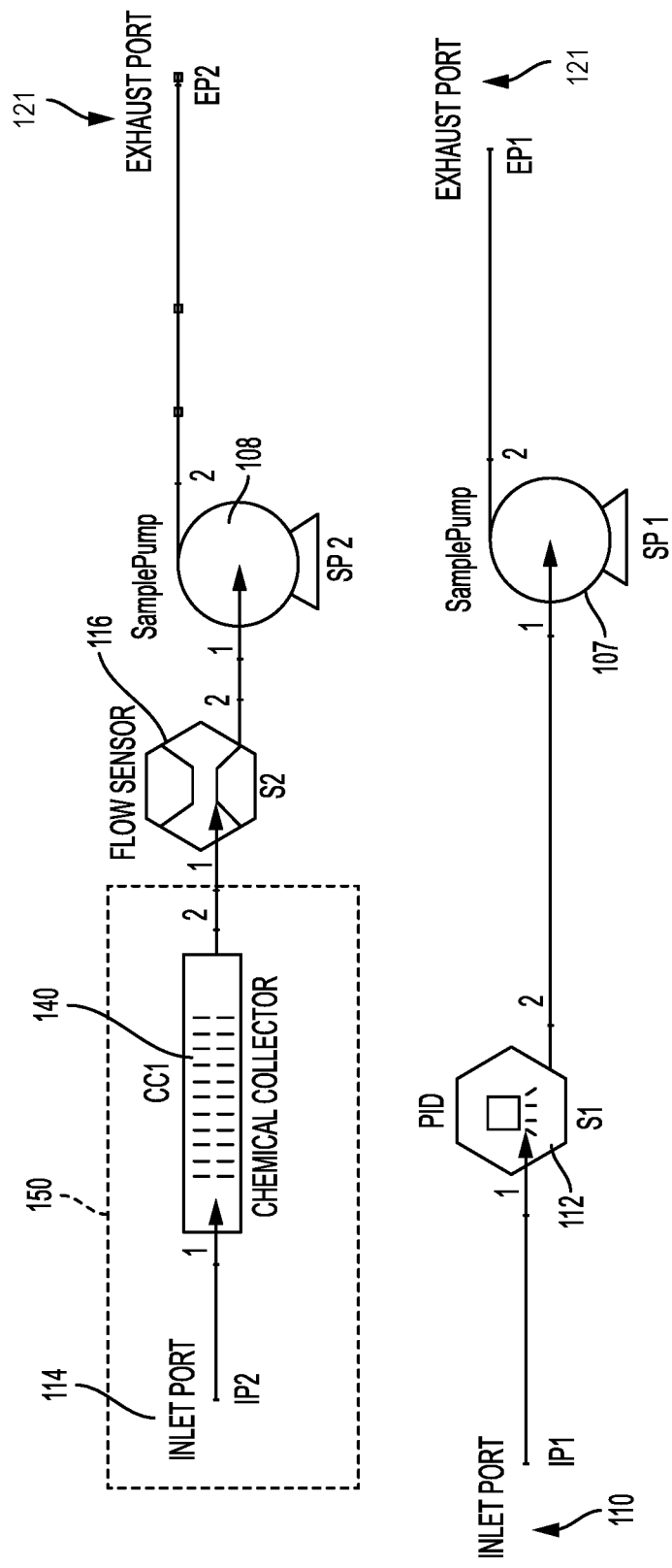
FIG. 6 is a flow schematic illustrating operation of a sample collection cartridge and a photoionization detector (PID) in a sample collection probe with separate exhaust ports in accordance with an embodiment.

Referring to FIG. 6, the HD module 112 is in a fluidic path in the sample collection probe 100 that is parallel to the fluidic path of the sample collection cartridge 150. In an embodiment, the second sample pump 107 pulls air through the PID module 112 such that the activities of measuring vapor concentrations with the PID module 112 and the sample collection onto the sample collection cartridge 150 can be controlled asynchronously. The microcontroller 113 receives current measurement from the PID module 112 and air flow sensor 116. In some embodiments, the flow measurement is made integral to the second sample pump 108, such as by measuring the frequency of a piston style sample pump.

Figure 7A:
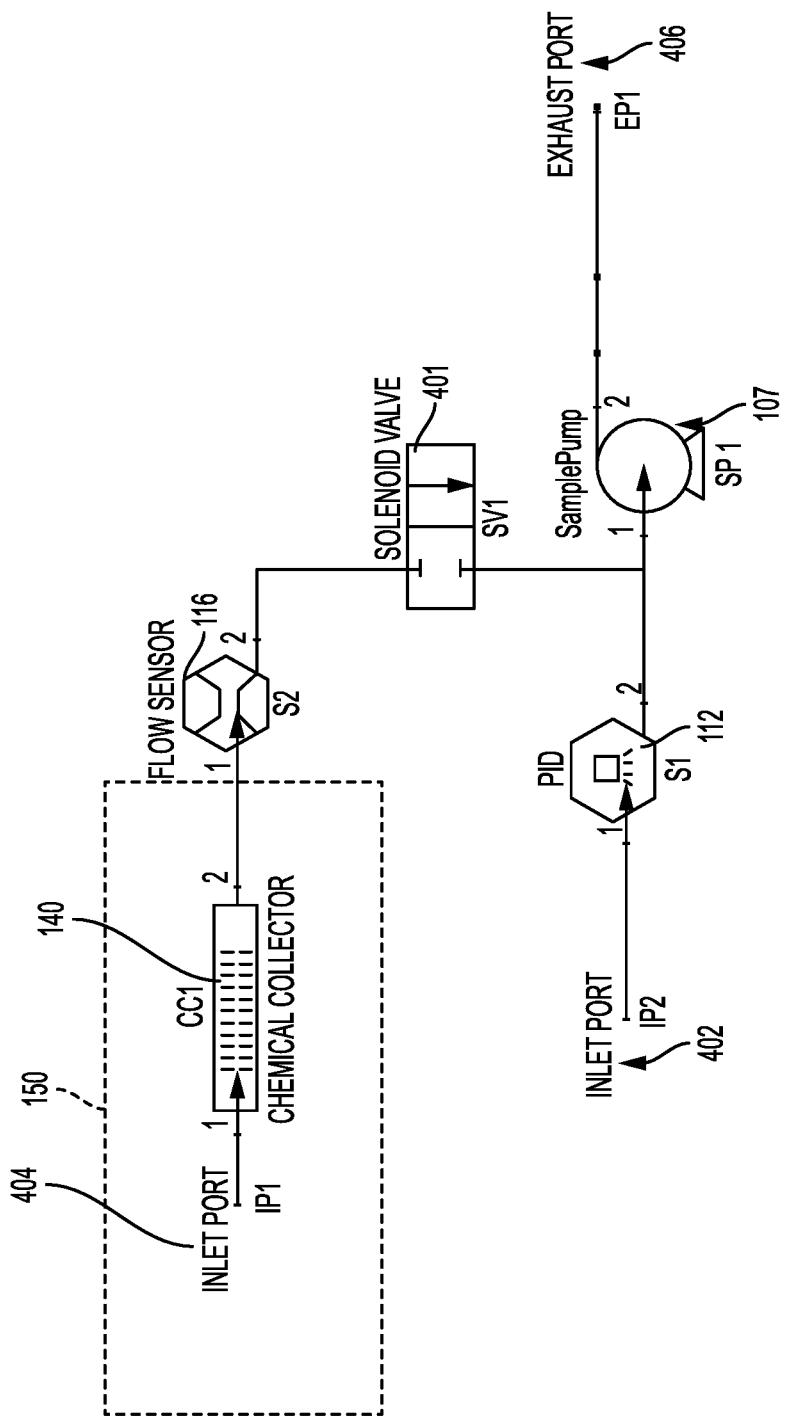
FIG. 7A is a flow schematic of a sample collection cartridge and a photoionization detector (PID) in a sample collection probe with only one sample pump used with the addition of a solenoid valve, in accordance with an embodiment.
Figure 7B:
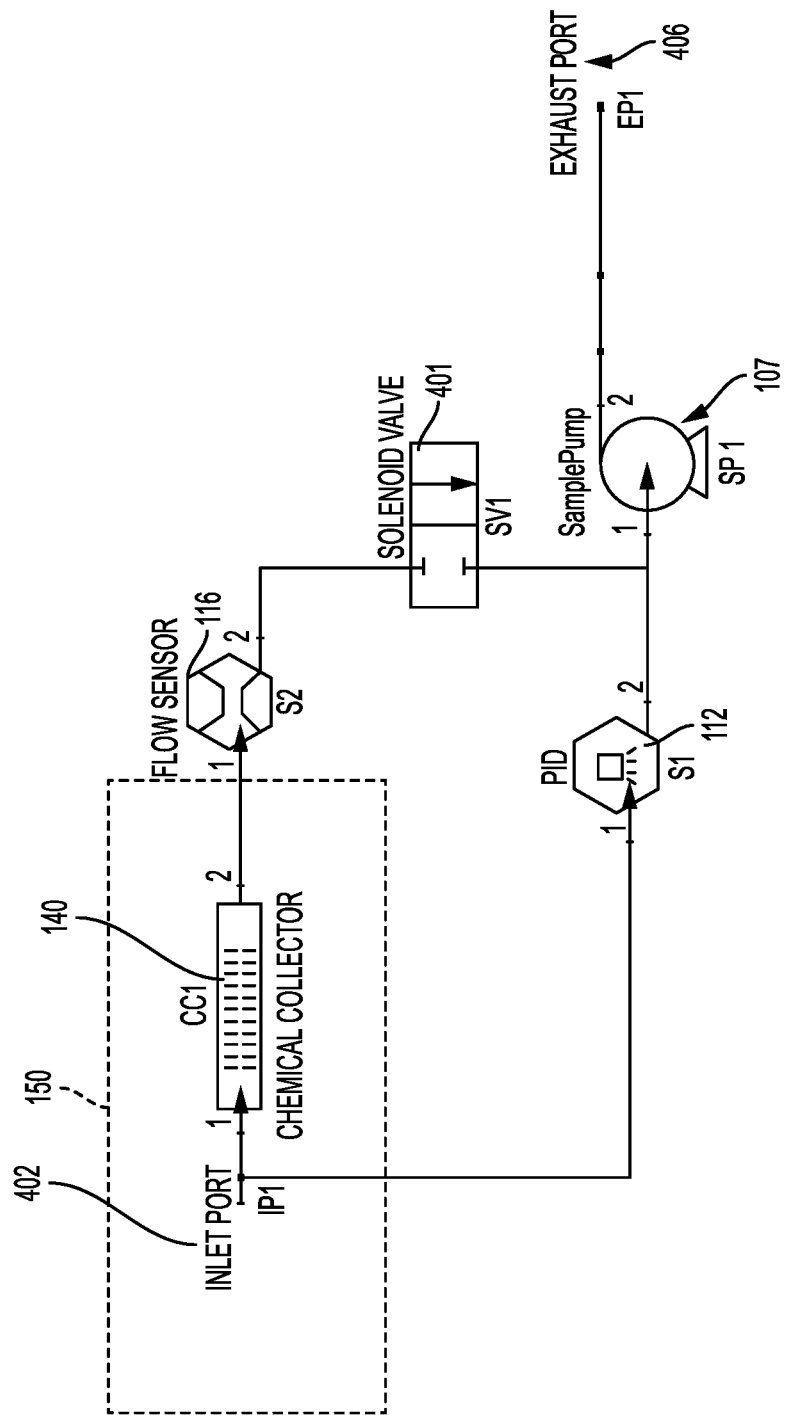
FIG. 7B is another flow schematic of a sample collection cartridge and a photoionization detector (PID) in a sample collection probe with only one sample pump used with the addition of a solenoid valve, in accordance with an embodiment.

FIGS. 7A and 7B illustrate alternative embodiments to the pneumatic arrangement described above. Instead of using two sample pumps 107, 108 in parallel fluidic paths, only one sample pump 107 is used with the addition of a solenoid valve 401. The sample pump 107 pulls the sample through the PID module 112 via the inlet port 402 and, when ready to draw air onto sample collection cartridge 150, the solenoid valve 401 actuates so that air is pulled through both pathways via the inlet port(s) 402, 404. Air exits through the exhaust port 406. The PID module 112 analyzes when the second sample pump 107 is running, although a sample only collects on the collection cartridge 150 when the solenoid valve 401 is actuated. This configuration maintains the ability to locate a sample and measure the real-time concentration of the sample with the PID module 112 and then independently choose to collect a mass of sample onto the sample collection cartridge 150 in the desired location. In another embodiment, referring now to FIG. 7B, the inlet to the PID module 112 and sample collection cartridge 150 share the same port 402. This port 402, which is located in a single opening in the housing, ensures that the sample analyzed by the PID module 112 accurately represents the collected sample.

Figure 8:
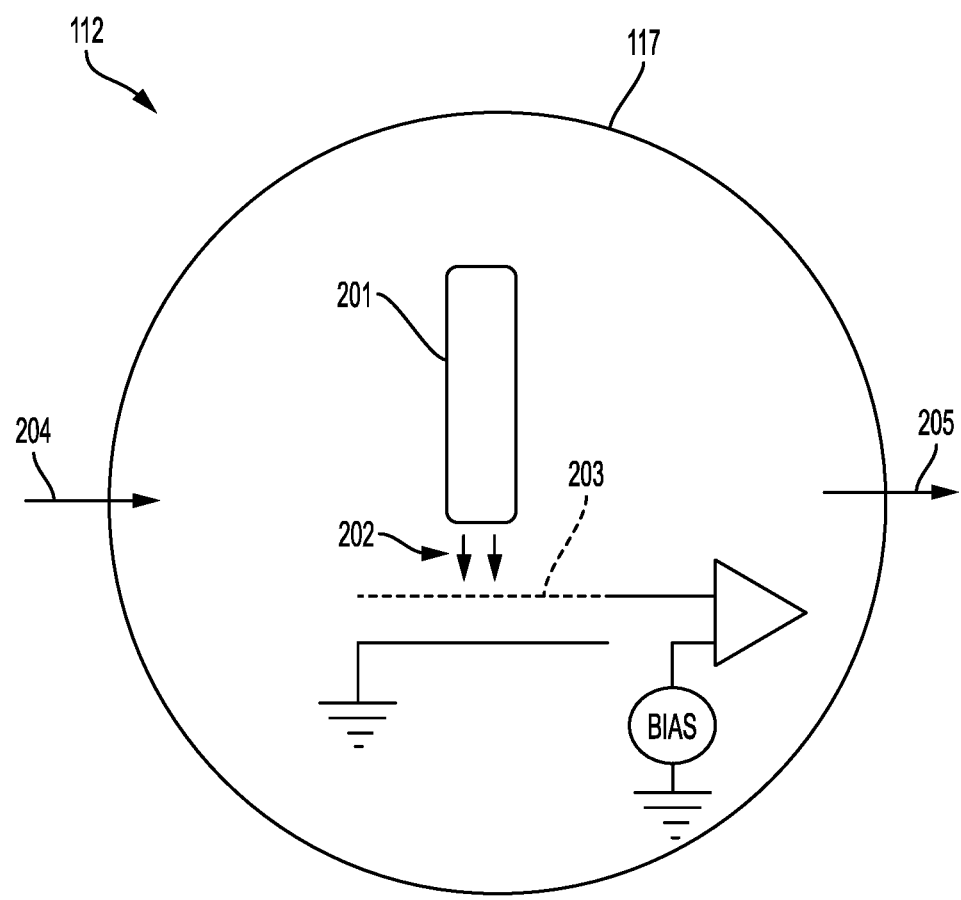
FIG. 8 is a schematic view of an embodiment of a Photo Ionization Detector (PID)

FIG. 8 illustrates an embodiment of a PID module 112. The PID module 112 includes a lamp 201 capable of producing high energy UV photons 202. The photons 202 ionize molecules, such as Volatile Organic Compounds (VOCs), with ionization energies lower than that of the photons 202, which is typically 10.6 eV. By applying an electric field, the resulting ions are measured on a faraday collector 203 from an air sample that is pulled through the PID housing 117 via an inlet port 204 and out through an exhaust port 205. Because most commonly-encountered VOCs ionize by this technique, the measured current is indicative of the total level of VOCs in an area of interest. The PID 112 responds to all photoionizable VOC compounds simultaneously and thus does not provide chemical identification. Because ionized compounds can have differing ionization efficiencies, PIDs are not used for definitive analysis of chemical vapors in air unless the single compound or the exact mole fraction of each compound in a mixture is known. However, ionization efficiencies and thus, the PID chemical sensitivity factors are sufficiently similar so as to generally inform a user regarding chemical concentration, even in embodiments where the identity of the chemical or chemicals is unknown.

The PID module 112 is subject to drift as the lamp window ages and also as the noble gases used to create the high energy photons 202 in a high voltage discharge are buried in the glass of the lamp 201, reducing the efficiency of the discharge. Accordingly, the PID module 112 is periodically recalibrated by connection of the probe opening 110 to the gas port 163 of the chemical analyzer 160. In an embodiment, this gas can be isobutylene, which is a common PID calibration gas, or it can be the same gases used to tune and calibrate the mass spectrometer in the analyzer, such as bromopentafluorobenzene.

Figure 12:
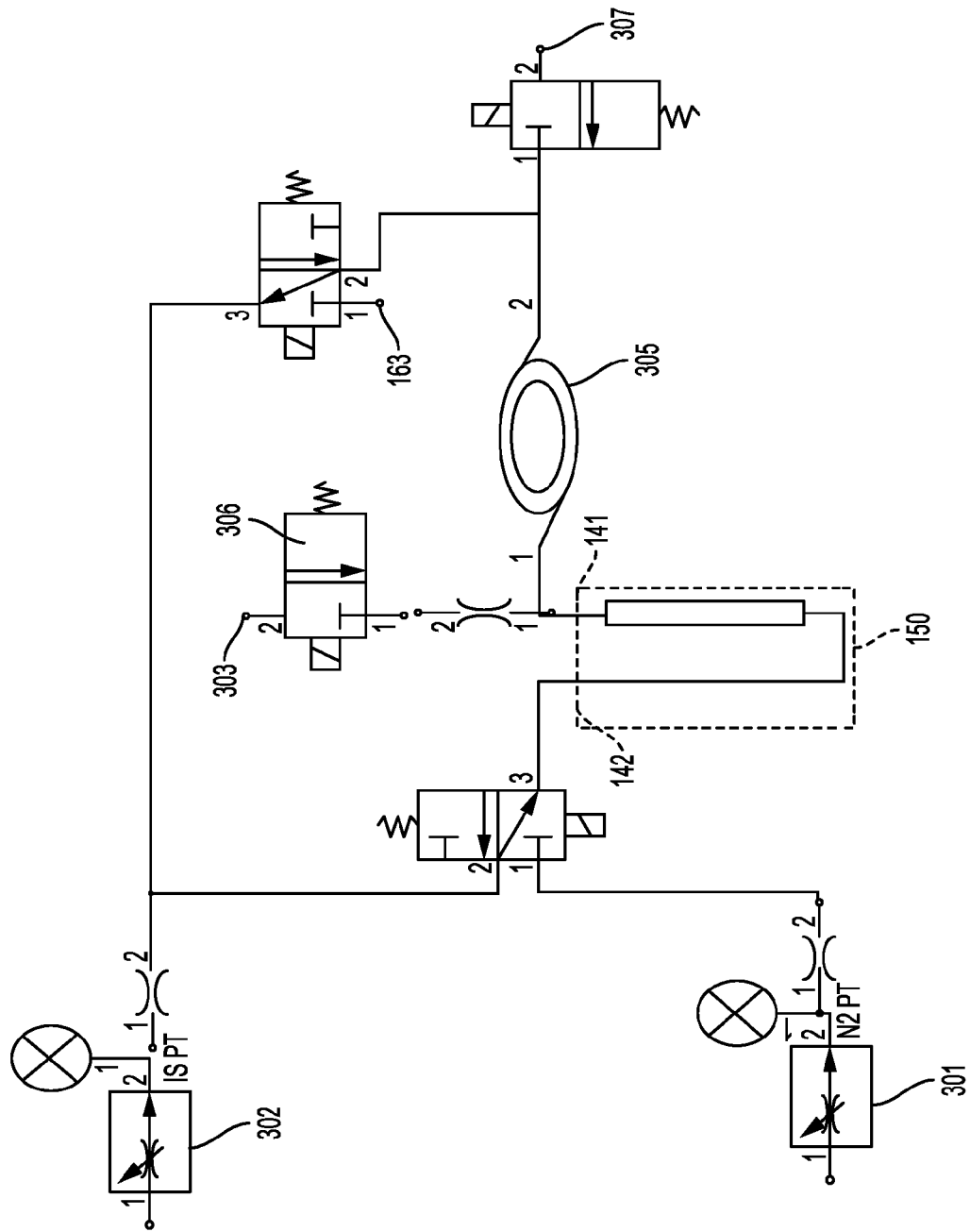
FIG. 12 is a gas chromatograph mass spectrometer flow schematic of a gas chromatograph mass spectrometer used to in conjunction with sample collection probe sampling in accordance with an embodiment.

This calibration method is illustrated in FIG. 12, which depicts a flow schematic for a GC/MS gas analyzer used to analyze the contents of the sample collection cartridge 150. Using the same gas to tune and calibrate both the MS and the gas sensor in the sample collection probe 100 reduces the need to carry additional gases to the field. The rate of tune gas delivery is controlled by a proportional valve 302. The ratio of this gas diluted with carrier gas from the proportional valve 301 permits a multipoint calibration of the MS (not shown) connected at a port 307 on the GC assembly and also multipoint calibration of the PID module 112 on the sample collection probe 100 by connection to the port 163 on the chemical analyzer 160. The calibration of the PID module 112, correlating current to concentration of the reference chemical, is stored on the sample collection probe 100. Thus, if the identity of a sample compound is known, its concentration can be calculated based on its sensitivity factor relative to the single reference chemical. The PID module 112 can provide accurate quantification when properly calibrated, but only for chemicals that are detectable by the PID module 112 and if the exact mix of chemicals is known. Nevertheless, handheld PID sensors are routinely used by first responders to make estimates of total hydrocarbon levels in hazmat scenarios. Even without knowing what chemicals they are looking for, responders find that a PID responds to the majority of VOCs and that PID sensitivity factors are similar for most VOCs. Thus, the PID provides a valuable estimate of total VOC concentration.

Referring again to FIG. 1, arrows depict a typical work flow. A sample (not shown) is collected on the sample collection cartridge 150 using the sample collection probe 100. The sample collection cartridge 150 is then decoupled from the sample collection probe 100 and coupled to the sample interface 162 (FIG. 2) of the chemical analyzer 160. After coupling to the chemical analyzer 160, the sample collection cartridge 150 is analyzed to provide information about the chemical contents of the sample. In an embodiment, the results of the analysis are displayed on the touch screen display 161. Following analysis, the sample collection cartridge 150 is decoupled from the chemical analyzer 160 and returned to the sample collection probe 100 to collect another sample.

For the chemical analyzer 160, there is an optimal mass of sample chemical that results in the best possible analysis (e.g., best SNR, linear response, etc.). The optimal sample mass can be established experimentally for a given chemical. In the embodiment of a GC/MS, there are two primary factors to assess the optimal amount of sample that should be collected for an analysis. The first of these factors is the maximum mass of sample that can be injected onto the column without causing degradation of chromatographic separation, which is determined based on the column dimensions and phase thickness, along with other characteristics. The second of these factors is related to the maximum mass for the MS analysis. This maximum mass depends on the individual levels of the chemicals because they are separated by the GC prior to MS analysis, and, more specifically, depends on the mass spectral fragmentation pattern resulting from electron impact ionization of the chemicals since it is the intensity of each fragment ion in a chemical that must be optimized for best performance on a MS. In this embodiment, it is important to collect a mass no higher than that which maximizes performance for the most intense ion. Other chemical analyzers have other factors that influence the optimal sample mass. To optimize sample collection, the sample collection probe 100 improves on traditional collection techniques by locating a sample source and estimating the mass collected, instead of relying on field personnel to collect based on sampling time or volume. In current practice, field personal are required to collect multiple samples in order to obtain one that has an amount of sample suitable for the analyzer. This multiple sample collection puts field personal at undue harm as they must spend longer periods in potentially dangerous environments.

Regardless of the analysis method, optimal sample mass of a chemical can be established empirically and these values compiled into a reference table stored on the memory 118 (FIG. 5) of the sample collection probe. If a user has some indication of the primary chemical of concern that may being collected, the user can input the chemical name(s) and the sample collection probe 100 will identify the target mass of sample to collect. The reference table of optimal sample masses permits the use of a "chemical scenario library". This "chemical scenario library" includes, for example, paint fumes, a gas spill, or a CWA event, among others. Each scenario has a preprogrammed set of N common chemicals and estimated mole fraction X of those chemicals.

Figure 9A:
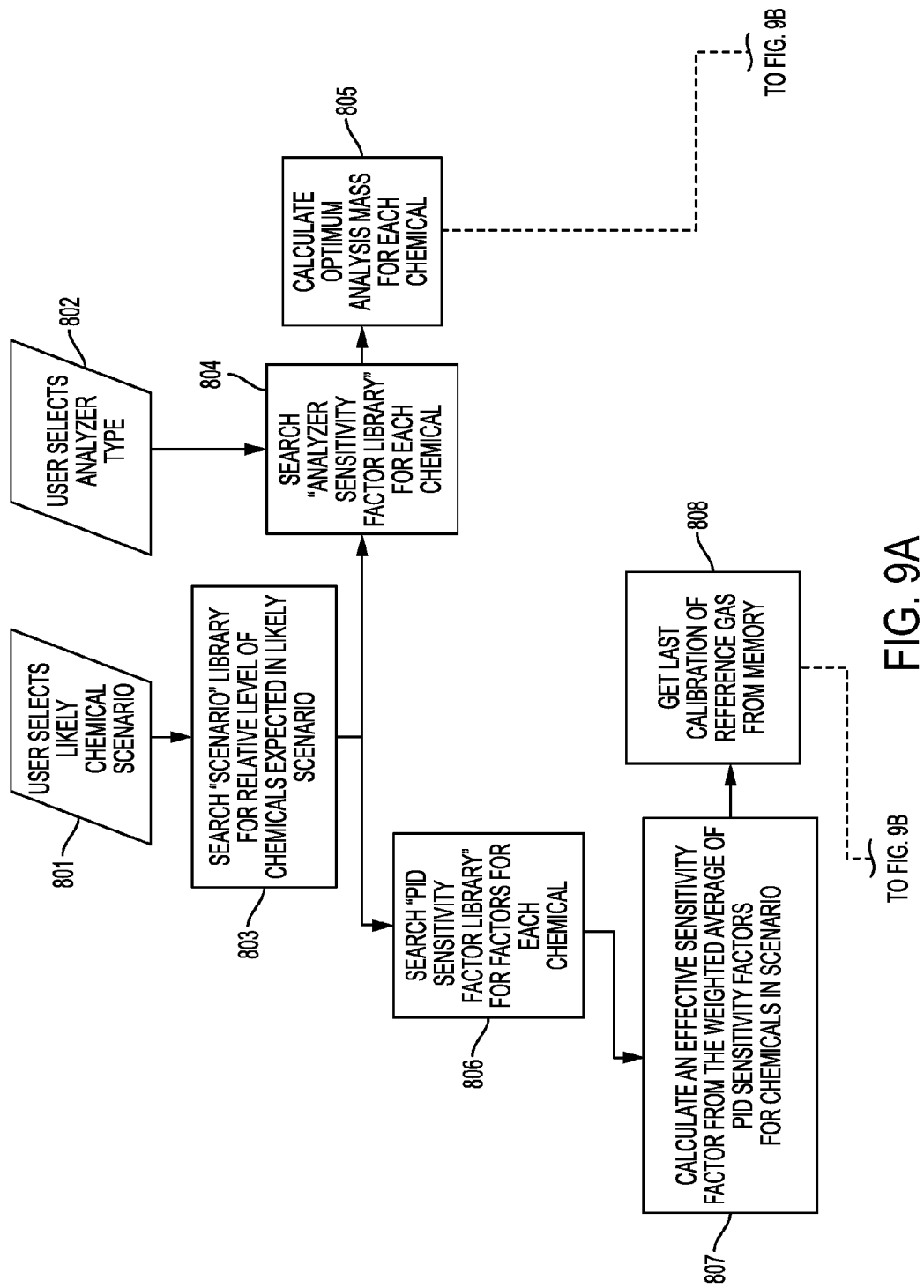
FIG. 9A is a flow diagram illustrating an embodiment of a chemical sample collection method.
Figure 9B:
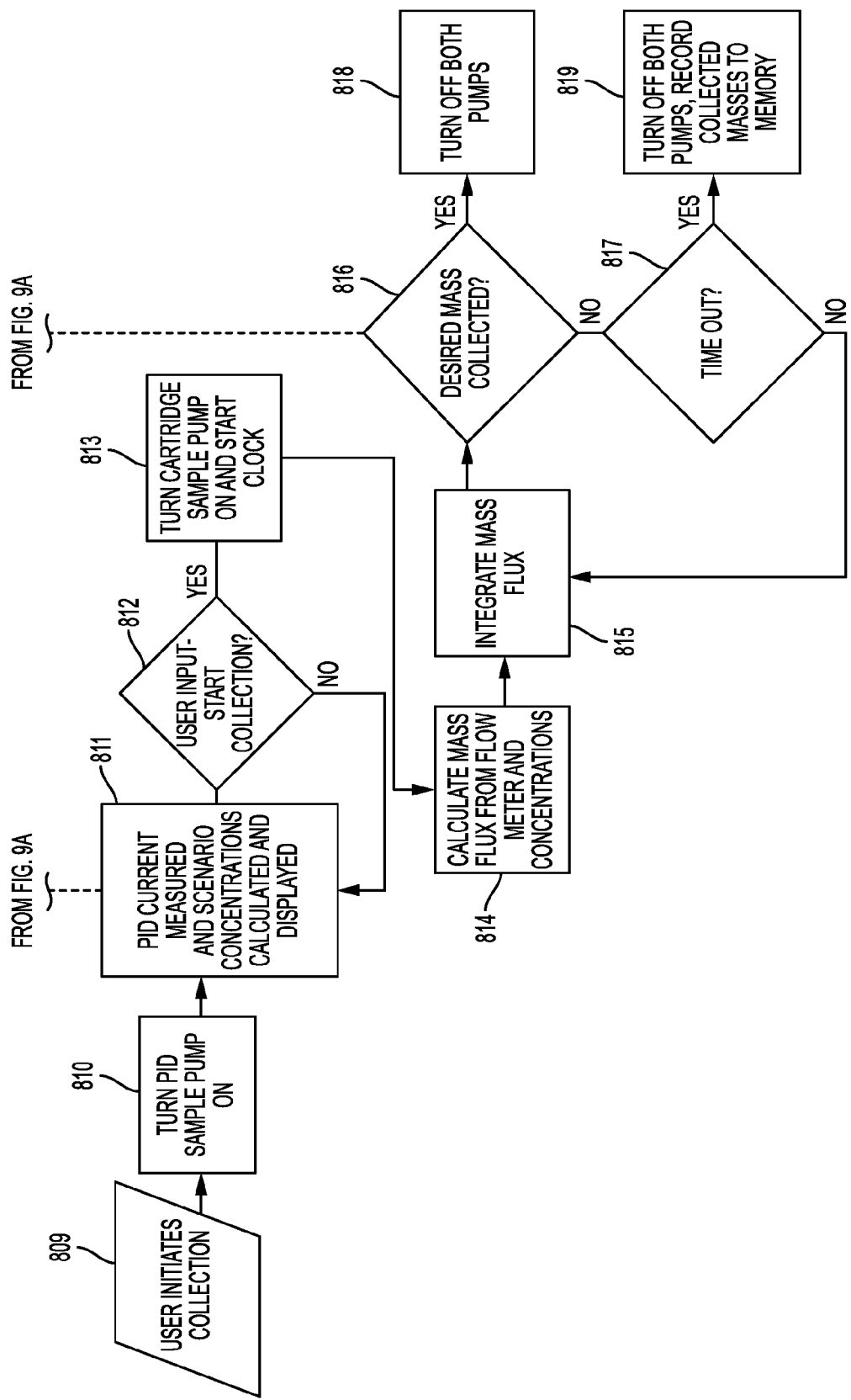
FIG. 9B is a continuation of the flow diagram of FIG. 9A.

FIGS. 9A and 9B illustrates an example of a method 800 for collecting the optimal sample mass using a chemical analysis system, such as the chemical analysis system 102 described above with regard to FIGS. 1-5, reference to which will be made in the following discussion when describing the actions of the components of the chemical analysis system 102. The method begins at block 801 with a user selecting a likely scenario from a chemical scenario library. At block 803, the chemical analyzer 160 (FIG. 2) searches a "scenario" library for relative levels of the chemicals expected to be in the scenario. At block 802, the user selects a chemical analyzer type that will be used to perform the eventual full chemical analysis. At block 804, the sample collection probe searches an "analyzer sensitivity factor library" for each chemical for the chosen analyzer. The analyzer could be analyzer 160. At block 805, the sample collection probe calculates the optimum analysis mass for each chemical. At block 806, the sample collection probe searches a "PID sensitivity factor library" to identify factors for each chemical. At block 807, the sample collection probe calculates the effective sensitivity factor from the weighted average of PID sensitivity factors for each chemical in the scenario and, at block 808, gathers the last calibration of reference gases from the memory in the sample collection probe. At block 809, the user initiates collection of the sample on the sample collection probe. The microcontroller 113 (FIG. 5) of the sample collection probe 100 turns on the PID module 112 and first sample pump 107 (block 810) and, at block 811, the microcontroller 113 measures the PID current and calculates scenario concentrations. At block 812, the sample collection probe 100 requests user input as to whether to start collection of the sample. If the user does not select ("no" branch of block 812) to start, the sample collection probe 100 will repeat block 811 until the user selects to start the collection. In repeating this block, the values measured by the PID are displayed to the user to help locate a good sampling location. If the user selects to start the collection ("yes" branch of block 812), at block 813, the microcontroller 113 turns on the pump 108 to pull the sample through the sample collection cartridge 150 and starts a timer. The microcontroller 113 then calculates the mass flux from the air flow sensor 116 and the concentrations collected by the PID module 112 (block 814) and, at block 815, integrates the mass flux. At block 816, the microcontroller 113 determines if the desired mass (the integral of the mass flux) is collected. If the desired mass is collected ("yes" branch of block 816), the microcontroller 113 turns off the pumps 107, 108 (block 818). If the desired mass is not collected ("no" branch of block 816), the microcontroller 113 determines if a timeout period has expired (block 817). If a timeout period has expired ("yes" branch of block 817), at block 819, the microcontroller 113 turns off the pumps and records the collected masses to memory 151. If a time out period has not expired ("no" branch of decision 817), the microcontroller 113 continues to integrate the mass flux (block 815) until the target mass is collected or the timeout condition occurs.

In an example, if a paint fumes scenario is selected on the sample collection probe interface, the scenario lists methyl ethyl ketone, acetone, and xylene at their respective mole fractions of 0.2:0.7:0.1, and also lists their sensitivity factors (SF). These N sensitivity factors are weighted by their expected mole fractions to generate a combined sensitivity factor ($SF_{total}$) that can be used to estimate the gas concentration of paint fumes from the PID response for each n chemical.

$$SF_{total} = \frac{1}{\sum_{n=1}^{N} \frac{X_n}{SF_n}}.$$

In this example, after the user initiates the probe 100 for sample collection as described above with regard to FIGS. 9A and 9B, a sample pump 107 connected to the PID module 112 turns on, and the current (I) is measured. The PID module 112 has been previously calibrated for its reference chemical as G=slope of concentration of the calibration chemical (g/L)/I (Amps). This permits the calculation of concentration C, independent of flow rate, for the scenario gas as $$C = SF_{total} * G * I.$$

Figure 10A:
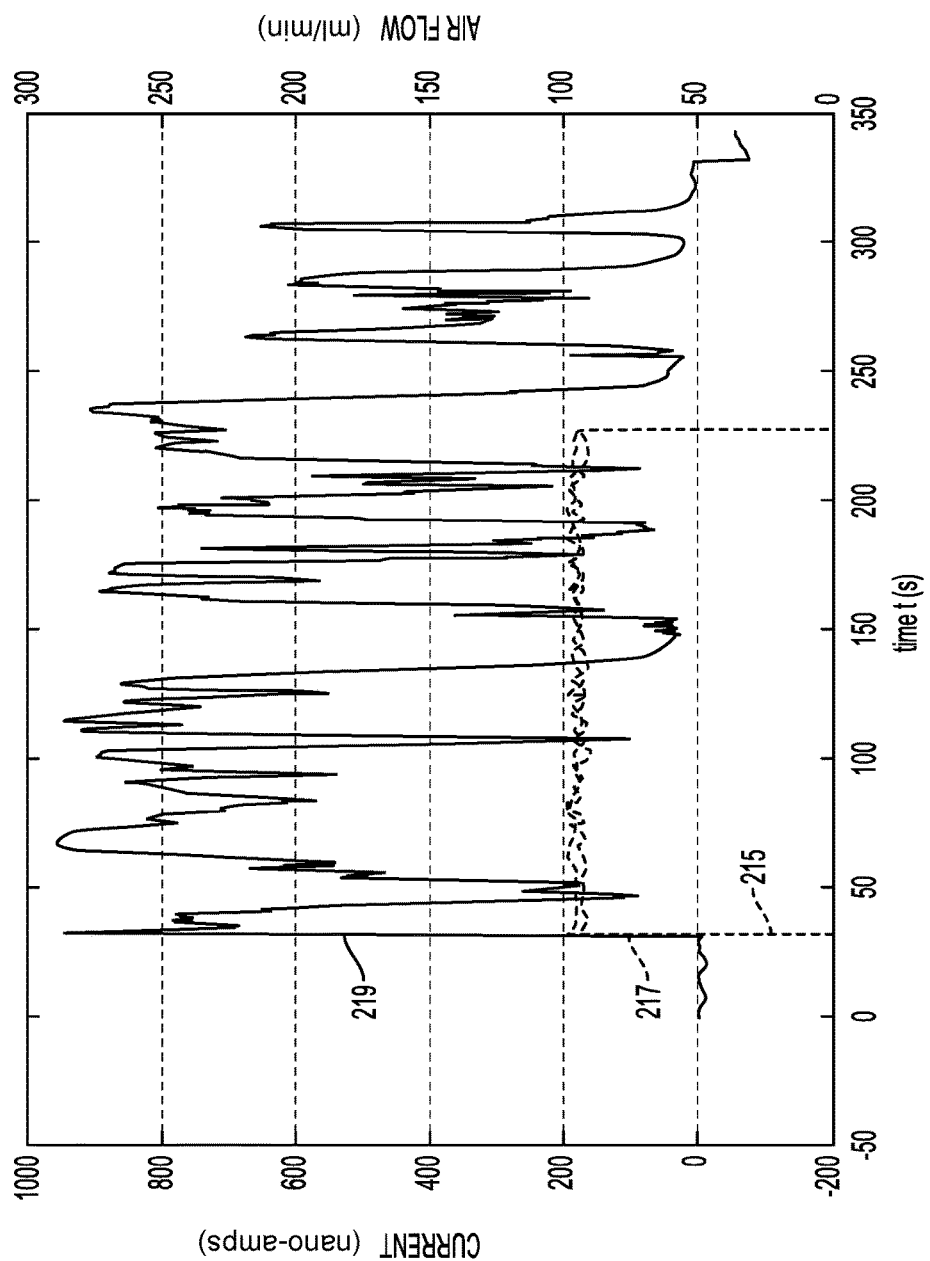
FIG. 10A is a graphical representation of PID current and measured gas flow rate through a sample cartridge, in accordance with an embodiment.

FIG. 10A is a graphical representation of PID current and measured gas flow through a sample cartridge 150 (FIGS. 3-4) in accordance with an embodiment. The solid line 219 in FIG. 10A is a plot of PID current I, measured as the sample collection probe 100 (FIG. 5) is moved into proximity to a vapor source. Fluctuations in the trace or line 219 indicate that the PID module 112 is experiencing a high degree of temporal variability in vapor phase concentration. After the current I, which corresponds to a vapor concentration, exceeds a minimum threshold 217, the sample pump 108 of the probe 100 is turned on, which causes air to flow though the sample collection cartridge 150. This increase in air flow upon turning on the sample pump 108, and the resultant air flow rate F, is shown as a dotted line 215. The microprocessor 113 records F 215 from the air flow sensor 116. The microcontroller 113 uses the instantaneous air flow rate F and the sensor current I to calculate mass flux φ of the sample retention device 140.

$$\varphi\left(\frac{mass}{second}\right) = SF_{total} * G * I * F$$

Figure 10B:
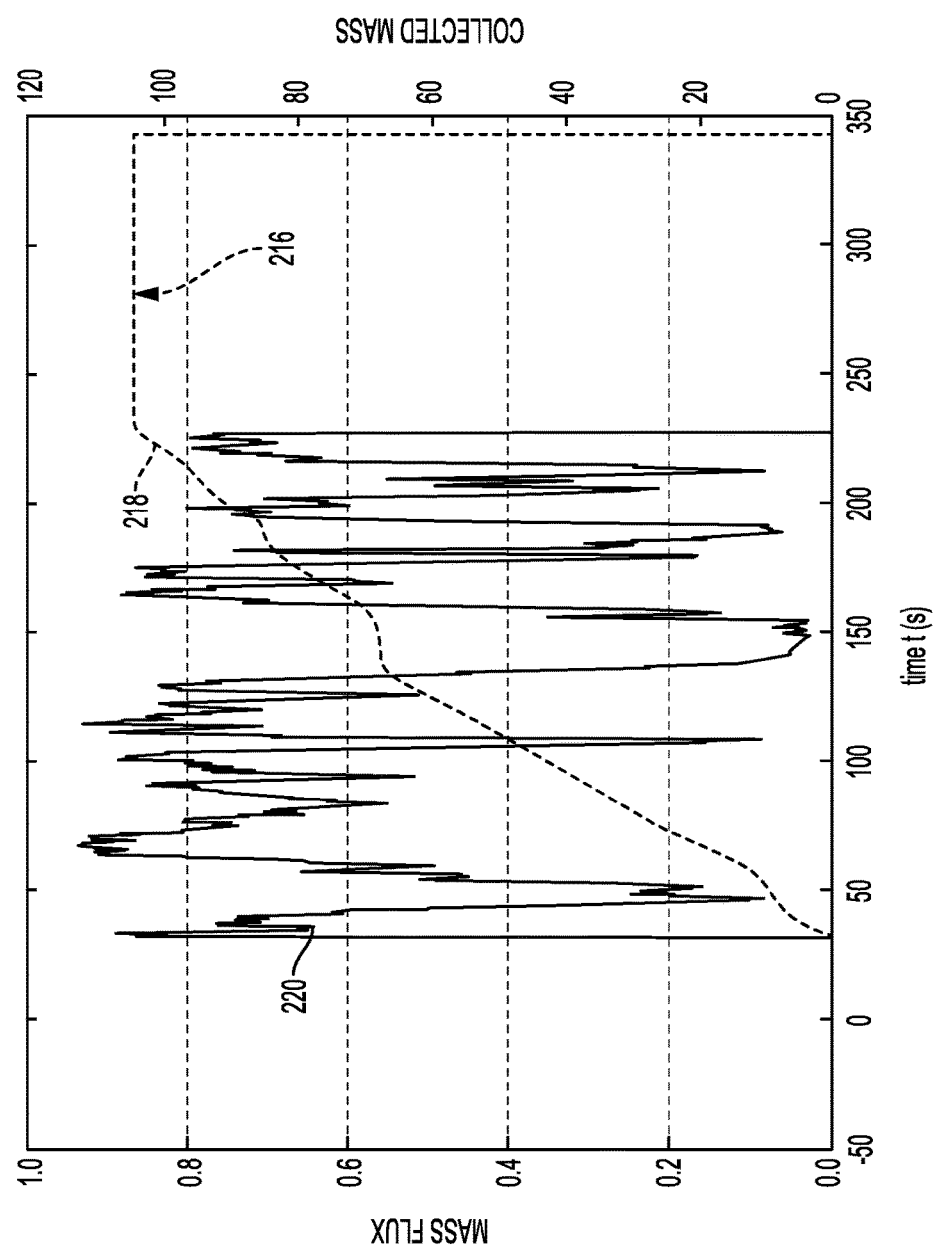
FIG. 10B is a graphical representation of mass flux calculated from PID current and the integral of mass flux in a sampling event in accordance with an embodiment.

Mass flux 220 and the integral of mass flux M 218 are displayed in FIG. 10B as solid and dotted lines respectively. The integral of the mass flux 218, which is the amount of mass collected in the sample collection cartridge 150 (FIGS. 3-4), is compared with target mass levels to optimize the eventual analysis. When the target mass 216 is collected, the sample pump 108 (FIG. 5) is shut off to complete the sample collection process.

The integral of instantaneous air flow rate (not shown) is the collected air sample volume, V. The probe 100 (FIG. 5) can also be programmed to stop sampling if excessive time or air flow has elapsed (i.e., timeout) without collecting the target mass. Excessive air flow could lead to break-through where a sample would no longer be captured by the adsorbent bed. The PID module 112 continues to run after the sample time, indicating chemical concentration in the area of the sample collection probe 100. Additional samples can be collected onto other cartridges 150 if better sample locations are identified.

Figure 11:
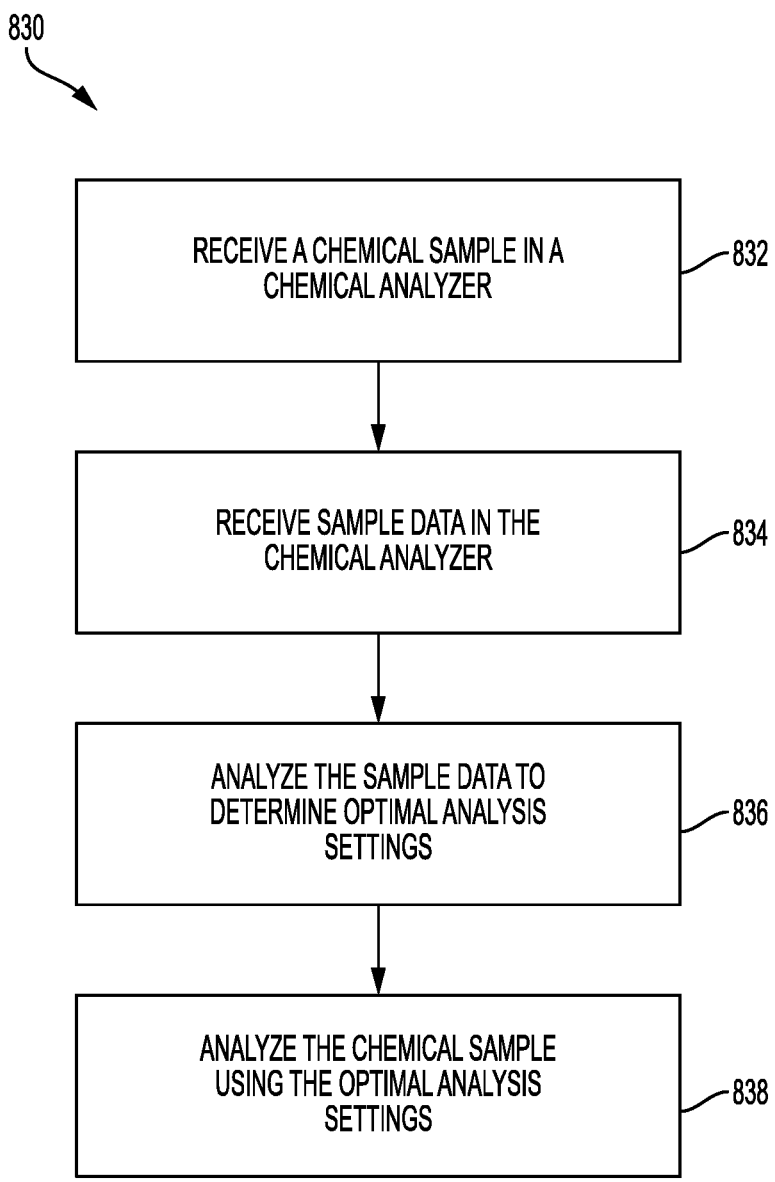
FIG. 11 is a flow diagram illustrating an embodiment of a chemical analysis method.

After collection of the sample, such as by the method 800 described in FIGS. 9A and 9B, the collected sample is analyzed. FIG. 11 illustrates an embodiment of a chemical analysis method 830. At block 832, the chemical sample is received in the chemical analyzer 160. For example, the sample is collected in the sample retention device 140 when the sample collection cartridge 150 is retained in the sample collection probe 100. Following collection of the sample, the sample collection cartridge 150 is decoupled from the probe 100 and coupled to the chemical analyzer 160.

At block 834, the sample data is received in the chemical analyzer 160. In an embodiment, the microcontroller 113 transmits the stored sample data, such as using a near field antenna 111, from the probe 100 to the sample collection cartridge 150, including calculated mass, total collected air sample volume, and measured concentration as a function of time. This data is received in the sample collection cartridge 150 via the antenna 147 (FIG. 3) and stored on a memory device 151. It will be obvious to those with experience in the fields of electronics that the drawings illustrate interconnections and relative placement of components rather than exact orientation of components, such as near field antennas 147 and 111 which must be largely parallel for efficient data transfer. The data is transmitted from the sample collection probe 100 to the sample collection cartridge 150, and from the sample collection cartridge 150 to the chemical analyzer 160. The sample collection cartridge 150 is transported to the chemical analyzer 160, and coupled physically and electronically to the chemical analyzer 160. The sample data is transmitted from the sample collection cartridge 150 to the chemical analyzer 160 using the near field communication antenna 147 or other communications interface. In an embodiment, the data is transmitted via near field communication. Wireless communication reduces the number of electrical connections on the exterior of the cartridge 150, thus reducing the number of vias through which the chemicals can penetrate to the sample collection probe 100 and chemical analyzer 160. These features reduce contamination and corrosion of electrical contacts during hazmat sampling scenarios.

Information about the collected sample dictates the analyzer settings. At block 836, a microcontroller (not shown) of the chemical analyzer 160 analyzes the sample data and determines the analyzer settings based on the sample data. If the target mass was collected, then the analysis proceeds with a default analytical method. If the target mass was not collected, the appropriate analyzer settings are changed dynamically to optimize the analysis, since there is only one opportunity to analyze the specific contents of a cartridge.

In an example, if a small integrated mass of sample was recorded during the sample interval, such as due to a timeout condition resulting from low air concentration, the microcontroller determines that a suboptimal amount of sample was collected. In this example, the recorded mass information is used to configure the MS electron multiplier to a higher bias voltage. A higher bias increases the gain, meaning that more secondary electrons are generated at the distal end of the multiplier for each collected ion. This increased gain compensates for a limited sample to provide improved Signal to Noise Ratio (SNR). If the electron multiplier was indiscriminately at the high bias required for low level samples, modest sample levels would saturate the electrometer or may produce nonlinearities in the electron multiplier (EM) output. Additionally, operating at a high electron multiplier bias causes suboptimal SNR and decreases the lifetime of the EM. The inverse correlation between EM voltage and estimated collected mass would be determined empirically prior to field use and programmed into the analyzer to enable the system to provide this compensation for higher or lower samples than those expected. Thus when the sample data is transferred to the chemical analyzer 160, the EM voltage is selected based on the estimated collected mass of sample. The mass is reported in equivalent units to the calibration gas. It will be obvious to those in the field of mass spectrometry that there are many other operating parameters that can be adjusted to improve SNR, linearity, or other performance metrics if information is available to estimate the size of the sample before performing an analysis on that sample.

If the estimated collected mass exceeds the target mass, the GC portion of the chemical analyzer 160 settings can also be modified to permit optimal analysis and prevent saturation of the chemical analyzer 160. The GC in FIG. 12 is designed to permit a split injection during the thermal desorption of the sample collection cartridge 150. A fraction of the sample is sent to a waste port 303 while a fraction is injected onto the column 305 by either adjusting the relative flows of these two pathways or by controlling at high frequency the on off/time of a diverting valve 306. For example, Pulse Width Modulation (PWM) can be used to send 95% of the sample to an exhaust vent. The mass recorded on a sample collection cartridge 150 during sample collection is used to establish the optimal split ratio, or PWM duty cycle, of the split valve, to provide the best SNR and other desired performance criteria, such as linearity, mass discrimination, and avoiding mass spectrometer saturation. If, for example, the total mass recorded on the sample collection cartridge 150 is ⅒th of the target collected mass, the split ratio could be adjusted from a normal 5% on column injection to 50% on column injection to keep the same mass injected onto the column and into the MS, which is connected to this GC system at port 307.

After the analysis settings are optimized, at block 838, the chemical analyzer 160 analyzes the chemical sample using the optimal analysis settings. In an example, the analysis process begins with heating the sample retention device 140 (e.g., adsorbent bed) using a heater coil 148 (FIG. 3). The heating coil 148 would not be necessary in all instances, such as when using the sample loop variant of the sample retention device 140. A carrier gas sweeps the sample through the port 141, onto the GC column 305. The chemicals elute from the column at different times and into the MS via port 307 for analysis. Chemical analyzers, such as GCs and GC/MSs, are often calibrated with standard injections covering a range of masses such that the response is then reported in mass. This permits the average concentration C for each chemical at a site during the sampling interval to be calculated as the output mass from the GC/MS divided by the volume of sample air collected.

$$C_{avg} = \frac{M}{V}$$

Thus, low concentration mixtures and unknown chemicals at a contamination site can be remotely sampled by the sample collection probe 100 and optimally analyzed at a separate, safer location where each component is accurately identified and quantified. The sample collection probe 100 and dynamic optimization method provides substantial improvement and optimization in sample collection over unguided sampling. For example, the PID module 112 allows the user to find the contamination site. If separate handheld PID devices were used for finding vapor sources and sample collection, this does not permit accurate sample collection in many sampling environments given the high vapor concentration gradients experienced around many sources. In another example, in its simplest sample collection mode, the sample collection probe 100 makes use of a simple empirical relationship between PID calibration gases and MS response to collect a target mass, even if this mass is in equivalent mass units of the calibration gas. Without applying sensitivity factors, the PID reports unknown vapor concentrations in the units (mass/volume) equivalent to the response of the calibration gas, where the error is given by the sensitivity factor of the unknown gas relative to the calibration gas. For example, collecting 100 ng of a VOC or mix of VOCs using a PID calibrated to isobutylene produces better analysis results than blind sampling, which may have collected less than 1 ng or more than 10,000 ng of sample. The error introduced by not knowing exactly which PID sensitivity factors to use is sufficiently small that this approach still optimizes sample collection in most VOC scenarios. Of course, it is possible to calibrate a PID with other gases, including scenario gases themselves (e.g, if an operator needs to detect and analyze paint fumes, they could calibrate the PID using paint fumes). In another example, if scenario information is available, the scenario library stored on the sample collection probe provides a further improvement over merely collecting a quantity of sample in units of mass relative to the calibration gas. In some situations, the mass collected can be very accurate since a reasonable assumption can be made about the sample identity (based on knowledge of the sample site). There is no guarantee, however, that the estimated collected mass will be exact. It is possible that, for example, some VOCs that are detectable by the PID module 112 will not be retained by the adsorbent material in the sample collection cartridge 150. In another example, a particular contaminant is not detectable by the PID module 112 but is retained by the adsorbent material. In the former example, the actual mass collected would be less than the estimate; in the latter, the actual mass collected would be greater than estimated. Because of these uncertainties, best operation of the sample collection sampling system 102 is to collect a target mass at the middle of the dynamic range of the chemical analyzer 160.

Data from the PID module 112 can also be used to determine if and how to decontaminate the sample collection probe 100 and the sample collection cartridge 150. If, for example, the PID module 112 response exceeds a concentration threshold prior to sample collection, sampling can be avoided to reduce the chances of contamination. If a high level above the contamination threshold is encountered during sampling, the sample collection cartridge 150 is considered contaminated and a prescribed decontamination technique is carried out prior to removing the sample collection cartridge 150 from the hazmat hot zone.

The start and stop processes can involve user interventions or can be automated to avoid or reduce operator error (e.g., the operator initiates an automated collection sequence, and the sample collection pump turns on and off as required to collect the correct amount of sample to optimize performance of the subsequent analysis). The automated collection sequences facilitate more advanced use embodiments, such as on a robot, drone, or other such remotely operated or autonomous vehicle. Additional connections (mounting features, and electrical) (not shown) on the sample collection probe 100 can enable integration onto these remote devices, minimizing human interaction required during sample collection.

A number of features ensure that the optimized sample meets various requirements for a documented chain of custody. These features can include a camera 101 to record features of the sample environment or digitize written notes, labels, and other markings. For example, the camera 101 (FIG. 5) records the labeling on a leaking tanker or bar codes on sample vials. A global positioning system (GPS) 112 is used to collect sample location and sampling path. Since the downstream chemical analyzer 160 makes only one integrated measurement of a collected sample, this path information combined with PID data can be used to determine the spatial concentration profile encountered by the sample collection probe 100 after the exact mix of chemicals is determined to allow more accurate interpretation of the PID data. This can be used to improve second sample collections, both in location and in mass collected, if additional sampling is required in the hazmat scenarios. Differential GPS 112 can provide accurate geospatial positioning, such as which exact chemical drum is the point source of a chemical hazard. The camera 101 on the sample collection probe 100 can also read bar codes or other markings such as concentrations or expiration dates of consumables used in the probe itself or in the analyzer.

Advantages of the above described system and devices include collecting a sample in the correct location to generate an accurate representation of the environment, including any point sources of chemical contamination. In addition, the system includes means to collect the quantity of sample vapor that best matches the analytical dynamic range of the particular analyzer for which the cartridge sample is intended, thereby providing optimal analytical performance. Furthermore, in embodiments where the optimal quantity of chemical sample cannot be collected, information is recorded in a memory device in the cartridge related to the amount of sample actually collected. This recorded information is transferred to the analyzer prior to analysis to adjust instrumental settings on the analyzer for optimization of the analysis of that cartridge sample.

It is not intended that the described embodiment is limiting. Alternate generally responsive chemical sensing detectors could be used in place of or in addition to the PD.

This written description uses examples to disclose the invention, including the best mode, and also to enable any person skilled in the art to practice the invention, including making and using any devices or systems and performing any incorporated methods. The patentable scope of the invention may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention is inclusive of combinations of the aspects described herein. Reference to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more tangible, non-transitory, computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

What is claimed is:

1. A chemical analysis system, comprising:
    a probe comprising:
        a photo ionization detector (PID) module configured to measure vapor concentration; and
        a microcontroller;
    a chemical analyzer; and
    a sample collection cartridge configured to removably couple to each of the probe and the chemical analyzer, respectively, the sample collection cartridge comprising:
        a sample retention device configured to store a chemical sample; and
        a memory,
    wherein the probe is configured to determine an optimal sample collection location,
    wherein when the sample collection cartridge is coupled to the probe, the probe is configured to collect a chemical sample in the sample collection cartridge and the microcontroller is configured to collect sample data during sample collection and store the sample data in the memory, and
    wherein when the sample collection cartridge is coupled to the chemical analyzer, the chemical analyzer is configured to determine optimal analysis settings based on the stored sample data and analyze the chemical sample using the determined optimal analysis settings.

2. The chemical analysis system of claim 1, wherein the sample data comprises total collected air sample volume, calculated sample mass, measured sample concentration, or a combination thereof.

3. The chemical analysis system of claim 1, wherein the probe is remote from the chemical analyzer.

4. The chemical analysis system of claim 1, wherein the chemical analyzer comprises a gas chromatograph/mass spectrometer.

5. The chemical analysis system of claim 1, wherein the sample retention device comprises a packed bed of sample collection media.

6. A probe for a chemical analyzer, comprising:
    a photo ionization detector (PID) module configured to measure vapor concentration of a chemical sample;
    a removable sample cartridge comprising an inlet port and a sample retention device;
    a sample pump operatively coupled to the removable sample cartridge and configured to draw a chemical sensor through the inlet port and into the sample retention device;
    a microcontroller; and
    a memory configured to store a reference table of target sample masses,
    wherein the microcontroller is configured to:
        determine an optimal sample collection location;
        monitor sample collection;
        determine sample data; and
        discontinue sample collection based on the sample data and the reference table.

7. The probe of claim 6, wherein the sample data comprises total collected air sample volume, calculated sample mass, measured sample concentration, or a combination thereof.

8. The probe of claim 6, wherein the probe is remote from the chemical analyzer.

9. The probe of claim 6, further comprising an air flow sensor.

10. The probe of claim 9, wherein the microcontroller is configured to receive a measured air flow rate from the air flow sensor; compare accumulated air flow to a reference table; and discontinue sample collection when excessive time or air flow has elapsed without collecting a target mass of sample.

11. The probe of claim 9, wherein the microcontroller is configured to receive a current from the PID module and an air flow rate from the air flow sensor; determine a collected sample mass based on the current and air flow rate; compare the collected sample mass to a target mass selected from the reference table; and discontinue sample collection when the collected sample mass matches the selected target mass.

12. A method of optimizing chemical sample analysis with a chemical analysis system comprising a probe, a sample collection cartridge, and a chemical analyzer, the probe comprising a photo ionization detector (PID) module and a microcontroller and the sample collection cartridge comprising a sample retention device and a memory, the method comprising:
    locating, via the PID module, an optimal sample collection location;
    collecting and storing a chemical sample in the retention device when the sample collection cartridge is retained within the probe;
    collecting, via the microcontroller, sample collection data; and
    storing the sample collection data in the memory.

13. The method of claim 12, wherein the sample data comprises total collected air sample volume, calculated sample mass, measured sample concentration, or a combination thereof.

14. The method of claim 12, further comprising:
    transmitting the sample data from the memory to the chemical analyzer when the sample collection cartridge is coupled to the chemical analyzer;
    determining, based on the sample collection data, optimal analysis settings of the chemical analyzer; and
    analyzing the chemical sample using the chemical analyzer at the optimal analysis settings.

15. The method of claim 14, further comprising reconstructing sample information based upon location information and recorded PID data.

16. The method of claim 14, wherein determining the optimal analysis settings comprises determining if a target sample mass was collected.

17. The method of claim 16, wherein if the target sample mass was collected, the optimal analysis setting of the chemical analyzer is a default setting.

18. The method of claim 16, wherein if the target sample mass was not collected, determining the optimal analysis settings comprises modifying analysis settings to compensate for a difference between a collected sample mass and the target sample mass.

19. The method of claim 12, further comprising calibrating the PID module based on a reference chemical, the reference chemical comprising an analyzer tuning gas.

20. The method of claim 12, further comprising determining a spatial concentration profile encountered by the probe based on PID data and location data.

* * * * *